(12) United States Patent
Banholzer et al.

(10) Patent No.: US 7,851,483 B2
(45) Date of Patent: *Dec. 14, 2010

(54) MEDICAMENTS COMPRISING STEROIDS AND A NOVEL ANTICHOLINERGIC

(75) Inventors: Rolf Banholzer, Stuttgart (DE); Helmut Meissner, Ingelheim (DE); Gerd Morschhaeuser, Biberach (DE); Michael P. Pieper, Biberach (DE); Gerald Pohl, Biberach (DE); Richard Reichl, Gau-Algesheim (DE); Georg Speck, Ingelheim am Rhein (DE); Christopher John Montague Meade, Maselheim (DE); Michel Pairet, Biberach (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 1138 days.

This patent is subject to a terminal disclaimer.

(21) Appl. No.: 11/407,735

(22) Filed: Apr. 20, 2006

(65) Prior Publication Data

US 2006/0276441 A1 Dec. 7, 2006

Related U.S. Application Data

(63) Continuation of application No. 10/391,735, filed on Mar. 19, 2003, now Pat. No. 7,084,153.

(60) Provisional application No. 60/386,790, filed on Jun. 7, 2002.

(30) Foreign Application Priority Data

Apr. 12, 2002 (DE) .................. 102 16 429

(51) Int. Cl.
  *A61K 31/44* (2006.01)
  *A61K 31/56* (2006.01)
  *A01N 45/00* (2006.01)
  *A01N 43/42* (2006.01)

(52) U.S. Cl. ................ 514/291; 514/304; 514/169

(58) Field of Classification Search ............ 514/291, 514/304, 169, 91
See application file for complete search history.

(56) References Cited

U.S. PATENT DOCUMENTS

| | | | |
|---|---|---|---|
| 4,042,700 A | 8/1977 | Banholzer et al. | |
| 4,608,377 A | 8/1986 | Banholzer et al. | |
| 4,783,534 A | 11/1988 | Banholzer et al. | |
| 5,610,163 A | 3/1997 | Banholzer et al. | |
| 5,654,314 A | 8/1997 | Banholzer et al. | |
| 5,770,738 A | 6/1998 | Banholzer et al. | |
| 5,952,505 A | 9/1999 | Banholzer | |
| 6,486,321 B2 | 11/2002 | Banholzer | |
| 6,506,900 B1 | 1/2003 | Banholzer et al. | |
| 6,630,466 B2 | 10/2003 | Bozung | |
| 6,706,726 B2 | 3/2004 | Meissner et al. | |

(Continued)

FOREIGN PATENT DOCUMENTS

| | | |
|---|---|---|
| AU | 12188/99 B | 9/1992 |
| CA | 2 105 575 C | 9/1992 |
| CA | 2436540 A1 | 2/2007 |
| EP | 0823423 A1 | 11/1998 |
| ES | 2 160 577 | 11/2001 |
| WO | 92/16528 A1 | 10/1992 |
| WO | 0178745 A1 | 10/2001 |
| WO | WO 01/78746 | 10/2001 |

(Continued)

OTHER PUBLICATIONS

Balzano, Giovanni, et al; Effectiveness and Acceptability of a Domiciliary Multidrug Inhalation treatment in Elderly Patients with Chronic Airflow Obstruction: Metered Dose Inhaler Versus Jet Nebulizer; Journal of Aerosol Medicine (2000) vol. 13, No. 1 pp. 25-33.

(Continued)

*Primary Examiner*—Yong S Chong
(74) *Attorney, Agent, or Firm*—Michael P. Morris; Wendy A. Petka

(57) ABSTRACT

A pharmaceutical composition comprising:
(a) a salt of formula 1

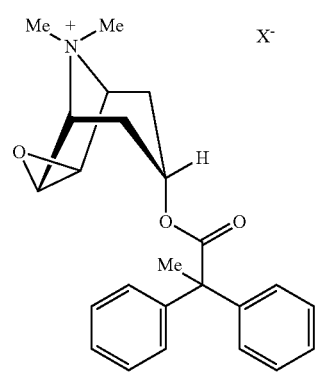

wherein:
X⁻ is an anion with a single negative charge; and
(b) a steroid 2,
processes for preparing such pharmaceutical composition, and their use in the treatment of respiratory complaints.

16 Claims, 3 Drawing Sheets

U.S. PATENT DOCUMENTS

| | | |
|---|---|---|
| 6,747,154 B2 | 6/2004 | Brandenburg et al. |
| 2002/0115681 A1 | 8/2002 | Bozung et al. |
| 2002/0133010 A1 | 9/2002 | Banholzer et al. |
| 2004/0002502 A1 | 1/2004 | Banholzer et al. |
| 2004/0010003 A1 | 1/2004 | Banholzer et al. |
| 2004/0024007 A1 | 2/2004 | Pairet et al. |
| 2004/0044020 A1 | 3/2004 | Meade et al. |
| 2004/0048886 A1 | 3/2004 | Meade et al. |
| 2004/0048887 A1 | 3/2004 | Meade et al. |
| 2004/0058950 A1 | 3/2004 | Meade et al. |
| 2004/0087617 A1 | 5/2004 | Meissner et al. |
| 2004/0166065 A1 | 8/2004 | Schmidt |
| 2004/0228805 A1 | 11/2004 | Pieper et al. |
| 2005/0004228 A1 | 1/2005 | Konetzki |
| 2005/0008578 A1 | 1/2005 | Schmidt |
| 2005/0025718 A1 | 2/2005 | Meade et al. |
| 2005/0101625 A1 | 5/2005 | Boeck et al. |
| 2005/0154006 A1 | 7/2005 | Meade et al. |
| 2005/0186175 A1 | 8/2005 | Meade et al. |

FOREIGN PATENT DOCUMENTS

| | | |
|---|---|---|
| WO | 0232899 A1 | 4/2002 |
| WO | WO 02/32899 | 4/2002 |
| WO | WO 02/36106 | 5/2002 |

OTHER PUBLICATIONS

Goodman & Gilman; The Phamacological Basis of Therapy; Ninth Edition, McGraw-Hil Interamericana, vol. 1, Mexico, pp. 163-164.

Ignatiev, V.A., et al; Comparative Study of efficacy of Combined Inhaled Brochodilators and Inhaled Corticosteroids During 12 Weeks Therapy in COPD Patients; European Respiratory Journal (1998) vol. 12, Suppl. 28 p. 40S.

Nishimura, Kiochi, et al; Additive Effect of Oxitropium Bromide in Combination with Inhaled Corticosteroids in the Treatment of Elderly Patients with Chronic Asthma; Allergology International (1999) vol. 48, No. 1 pp. 85-88.

MEDICAMENTS COMPRISING STEROIDS AND A NOVEL ANTICHOLINERGIC

RELATED APPLICATIONS

This application is a continuation of U.S. Ser. No. 10/391,735, filed Mar. 19, 2003, now U.S. Pat. No. 7,084,153, issued Aug. 1, 2006, which claimed benefit of U.S. Ser. No. 60/386,790, filed Jun. 7, 2002.

FIELD OF THE INVENTION

The present invention relates to novel pharmaceutical compositions based on steroids with a long-lasting effect and salts of a new anticholinergic, processes for preparing them, and their use in the treatment of respiratory complaints.

BRIEF DESCRIPTION OF THE DRAWINGS

FIG. 2a shows a longitudinal section through the nebulizer with the spring biased, whereas FIG. 2b shows a longitudinal section through the nebulizer with the spring relaxed.

DESCRIPTION OF THE INVENTION

Figure 1:
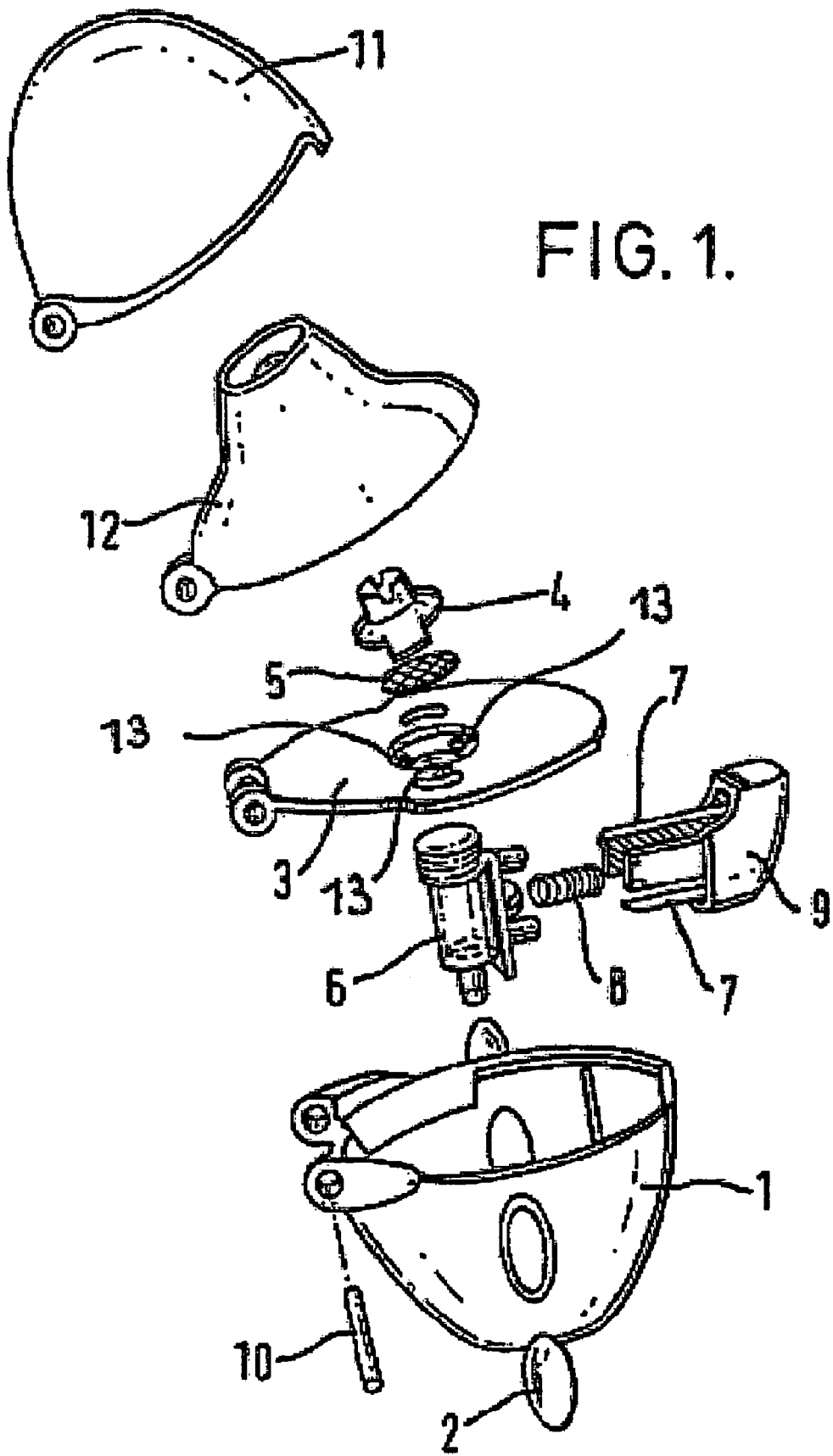
FIG. 1 illustrates an exploded view of a preferred inhaler for administration of a pharmaceutical combination described herein.

The present invention relates to novel pharmaceutical compositions based on steroids and salts of a new anticholinergic 1, processes for preparing them, and their use in the treatment of respiratory complaints.

Within the scope of the present invention, the anticholinergic agents used are the salts of formula 1

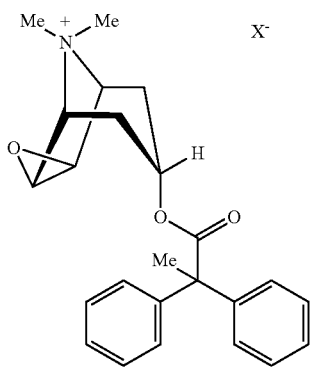

1 wherein:

$X^-$ denotes an anion with a single negative charge, preferably an anion selected from the group consisting of chloride, bromide, iodide, sulfate, phosphate, methanesulfonate, nitrate, maleate, acetate, citrate, fumarate, tartrate, oxalate, succinate, benzoate, and p-toluenesulfonate.

Preferably, the salts of formula 1 are used wherein $X^-$ denotes an anion with a single negative charge selected from among chloride, bromide, 4-toluenesulfonate, and methanesulfonate, preferably bromide.

Most preferably, the salts of formula 1 are used wherein $X^-$ denotes an anion with a single negative charge selected from among chloride, bromide, and methanesulfonate, preferably bromide.

Particularly preferred according to the invention is the salt of formula 1 wherein $X^-$ denotes bromide.

Anticholinergics may appropriately be used to treat a number of diseases. Particular mention should be made, for example, of the treatment of asthma or chronic obstructive pulmonary disease (COPD). For treating these diseases, WO 92/16528 proposes, for example, anticholinergics which have a scopine, tropenol, or tropine basic structure. The problem on which WO 92/16528 is based is the preparation of anticholinergically active compounds which are characterized by their long-lasting activity. To solve this problem, WO 92/16528 discloses inter alia benzilic acid esters of scopine, tropenol, or tropine.

For treating chronic diseases, it is often desirable to prepare pharmaceutical compositions with a longer-lasting effect. This will generally ensure that the concentration of the active substance needed to achieve the therapeutic effect is present in the body for a longer period of time without the need for the pharmaceutical composition to be administered repeatedly and all too frequently. Moreover, if an active substance is administered at longer intervals of time, this contributes to the feeling of well-being of the patient to a considerable degree. It is particularly desirable to provide a pharmaceutical composition which can be used to therapeutically good effect by administering it once a day (single dose). A single application per day has the advantage that the patient can become accustomed relatively quickly to the regular taking of the medicament at a particular time of the day.

If it is to be used as a medicament for administration once a day, the active substance which is to be given must meet particular requirements. First of all, the desired onset of the activity after the administration of the pharmaceutical composition should occur relatively quickly and ideally the activity should remain as constant as possible over a fairly lengthy ensuing period. On the other hand, the duration of activity of the pharmaceutical composition should not greatly exceed a period of about one day. Ideally, an active substance should have an activity profile such that the preparation of a pharmaceutical composition which is intended to be administered once a day and contains the active substance in therapeutically appropriate doses can be properly controlled.

It has been found that the esters of scopine, tropenol, or tropine disclosed in WO 92/16528 do not meet these more stringent requirements. Because of their extremely long duration of activity, significantly exceeding the period of about one day specified above, they cannot be used therapeutically in a single once-a-day dose.

Surprisingly, an unexpectedly beneficial therapeutic effect, particularly a synergistic effect is observed in the treatment of inflammatory or obstructive diseases of the respiratory tract if the anticholinergic of formula 1 is used with one or more, preferably one, steroid 2. In view of this synergistic effect the pharmaceutical combinations according to the invention can be used in smaller doses than would be the case with the individual compounds used in monotherapy in the usual way. Furthermore, this reduces unwanted side effects such as may occur when steroids are administered, for example.

The effects mentioned above may be observed both when the two active substances are administered simultaneously in a single active substance formulation and when they are administered successively in separate formulations. According to the invention, it is preferable to administer the two active substance ingredients simultaneously in a single formulation. The pharmaceutical compositions according to the invention are preferably administered by inhalation.

Within the scope of the present invention, any reference to the compound 1' is to be regarded as a reference to the pharmacologically active cation of the following formula contained in the salts 1:

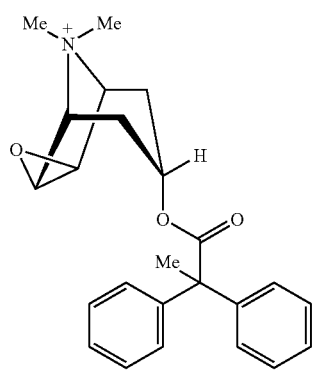

Any reference to compounds 1 naturally also includes a reference to the cation 1'.

In the pharmaceutical combinations mentioned above the active substances 1 and 2 may be combined in a single preparation or contained in two separate formulations. Pharmaceutical compositions which contain the active substances 1 and 2 in a single preparation are preferred according to the invention.

Within the scope of the present invention, the term steroids (hereinafter 2), which are optionally also referred to as corticosteroids, denotes compounds selected from among flunisolide, beclomethasone, triamcinolone, budesonide, fluticasone, mometasone, ciclesonide, rofleponide, ST-126, and dexamethasone. Preferably, the compound 2 is selected from among budesonide, fluticasone, mometasone, ciclesonide, and ST-126.

Any reference to steroids 2 within the scope of the present invention includes a reference to the salts or derivatives which may be formed from the steroids. Examples of possible salts or derivatives include: sodium salts, sulfobenzoates, phosphates, isonicotinates, acetates, propionates, dihydrogen phosphates, palmitates, pivalates, or furoates. In some cases, the compounds of formula 2 may also occur in the form of their hydrates. Any reference to steroids 2 within the scope of the present invention also includes a reference to the compounds 2 in the form of their diastereomers, mixtures of diastereomers, or in the form of the racemates.

In one aspect the present invention relates to the abovementioned pharmaceutical compositions which contain, in addition to therapeutically effective quantities of 1 and 2, a pharmaceutically acceptable carrier. In another aspect the present invention relates to the abovementioned pharmaceutical compositions which do not contain any pharmaceutically acceptable carrier in addition to therapeutically effective quantities of 1 and 2.

The present invention also relates to the use of therapeutically effective quantities of the salts 1 for preparing a pharmaceutical composition also containing steroids 2 for treating inflammatory or obstructive diseases of the respiratory tract. Preferably, the present invention relates to the abovementioned use for preparing a pharmaceutical composition for treating asthma or COPD.

Within the scope of the present invention the compounds 1 and 2 may be administered simultaneously or successively, while it is preferable according to the invention to administer compounds 1 und 2 simultaneously.

The present invention further relates to the use of therapeutically effect amounts of salts 1 and steroids 2 for treating inflammatory or obstructive respiratory complaints, particularly asthma or COPD.

The proportions in which the active substances 1 and 2 may be used in the active substance combinations according to the invention are variable. Active substances 1 and 2 may possibly be present in the form of their solvates or hydrates. Depending on the choice of the compounds 1 and 2, the weight ratios which may be used within the scope of the present invention vary on the basis of the different molecular weights of the various compounds and their different potencies. As a rule, the pharmaceutical combinations according to the invention may contain the cation 1' and a steroid 2 in ratios by weight ranging from 1:250 to 250:1, preferably from 1:150 to 150:1. In the particularly preferred pharmaceutical combinations which contain in addition to 1' a compound selected from among the group consisting of budesonide, fluticasone, mometasone, ciclesonide, and ST-126 as the steroid 2, the weight ratios of 1' to 2 are most preferably in a range from about 1:40 to 40:1, more preferably from 1:30 to 30:1.

For example, without restricting the scope of the invention thereto, preferred combinations of 1 and 2 according to the invention may contain the cation 1' and one of the abovementioned preferred steroids 2 in the following weight ratios: 1:20; 1:19; 1:18; 1:17; 1:16; 1:15; 1:14; 1:13; 1:12; 1:11; 1:10; 1:9; 1:8; 1:7; 1:6; 1:5; 1:4; 1:3; 1:2; 1:1; 2:1; 3:1; 4:1; 5:1; 6:1; 7:1; 8:1; 9:1; 10:1; 11:1; 12:1; 13:1; 14:1; 15:1; 16:1; 17:1; 18:1; 19:1; and 20:1.

The pharmaceutical compositions according to the invention containing the combinations of 1 and 2 are normally administered so that 1' and 2 are present together in doses of 5 μg to 5000 μg, preferably from 10 μg to 2000 μg, more preferably from 15 μg to 1000 μg, better still from 20 μg to 800 μg, preferably, according to the invention, from 30 μg to 700 μg, preferably from 40 μg to 600 μg, preferably from 50 μg to 550 μg, preferably from 40 μg to 500 μg, most preferably 50 μg to 400 μg per single dose. For example, combinations of 1 and 2 according to the invention contain a quantity of 1' and steroid 2 such that the total dosage per single dose is about 35 μg, 45 μg, 50 μg, 55 μg, 60 μg, 65 μg, 70 μg, 75 μg, 80 μg, 85 μg, 90 μg, 95 μg, 100 μg, 105 μg, 110 μg, 115 μg, 120 μg, 125 μg, 130 μg, 135 μg, 140 μg, 145 μg, 150 μg, 155 μg, 160 μg, 165 μg, 170 μg, 175 μg, 180 μg, 185 μg, 190 μg, 195 μg, 200 μg, 205 μg, 210 μg, 215 μg, 220 μg, 225 μg, 230 μg, 235 μg, 240 μg, 245 μg, 250 μg, 255 μg, 260 μg, 265 μg, 270 μg, 275 μg, 280 μg, 285 μg, 290 μg, 295 μg, 300 μg, 305 μg, 310 μg, 315 μg, 320 μg, 325 μg, 330 μg, 335 μg, 340 μg, 345 μg, 350 μg, 355 μg, 360 μg, 365 μg, 370 μg, 375 μg, 380 μg, 385 μg, 390 μg, 395 μg, 400 μg, 405 μg, 410 μg, 415 μg, 420 μg, 425 μg, 430 μg, 435 μg, 440 μg, 445 μg, 450 μg, 455 μg, 460 μg, 465 μg, 470 μg, 475 μg, 480 μg, 485 μg, 490 μg, 495 μg, 500 μg, 505 μg, 510 μg, 515 μg, 520 μg, 525 μg, 530 μg, 535 μg, 540 μg, 545 μg, 550 μg, 555 μg, 560 μg, 565 μg, 570 μg, 575 μg, 580 μg, 585 μg, 590 μg, 595 μg, 600 μg, 605 μg, 610 μg or similar. It is clear to anyone skilled in the art that the suggested dosages per single dose specified above are not to be regarded as being limited to the numerical values actually stated. Fluctuations of about ±2.5 μg, particularly in the decimal range, are also included, as will be apparent to one of skill in the art. In these dosage ranges, the active substances 1' and 2 may be present in the weight ratios given above.

For example, without restricting the scope of the invention thereto, the combinations of 1 and 2 according to the invention may contain a quantity of cation 1' and steroid 2 such that, for each single dose, 16.5 μg of 1' and 25 μg of 2, 16.5 μg of 1' and 50 μg of 2, 16.5 μg of 1' and 100 μg of 2, 16.5 μg of 1' and 150 μg of 2, 16.5 μg of 1' and 200 μg of 2, 16.5 μg of 1' and 250 μg of 2, 33.0 μg of 1' and 25 μg of 2, 33.0 μg of 1' and 50 μg of 2, 33.0 μg of 1' and 100 μg of 2, 33.0 μg of 1' and 150 μg of 2, 33.0 μg of 1' and 200 μg of 2, 33.0 μg of 1' and 250 μg of 2, 49.5 μg of 1' and 25 μg of 2, 49.5 μg of 1' and 50 μg of 2, 49.5 μg of 1' and 100 μg of 2, 49.5 μg of 1' and 150 μg of 2, 49.5 μg of 1' and 200 μg of 2, 49.5 μg of 1' and 250 μg of 2, 82.6 μg of 1' and 25 μg of 2, 82.6 μg of 1' and 50 μg of 2, 82.6 μg of 1' and 100 μg of 2, 82.6 μg of 1' and 150 μg of 2, 82.6 μg of 1' and 200 μg of 2, 82.6 μg of 1' and 250 μg of 2, 165.1 μg of 1' and 25 μg of 2, 165.1 μg of 1' and 50 μg of 2, 165.1 μg of 1' and 50 μg of 2, 165.1 μg of 1' and 100 μg of 2, 165.1 μg of 1' and 150 μg of 2, 165.1 μg of 1' and 200 μg of 2, 165.1 μg of 1' and 250 μg of 2, 206.4 μg of 1' and 25 μg of 2, 206.4 μg of 1' and 50 μg of 2, 206.4 μg of 1' and 100 μg of 2, 206.4 μg of 1' and 150 μg of 2, 206.4 μg of 1' and 200 μg of 2, 206.4 g of 1' and 250 μg of 2, 412.8 μg of 1' and 25 μg of 2, 412.8 μg of 1' and 50 μg of 2, 412.8 μg of 1' and 100 μg of 2, 412.8 μg of 1' and 150 μg of 2, 412.8 μg of 1' and 200 μg of 2, or 412.8 μg of 1' and 250 μg of 2 are present.

If the active substance combination in which the bromide is used as the salt 1 and in which 2 denotes one of the steroids mentioned above as being preferred is used as the preferred combination of 1 and 2 according to the invention, the quantities of active substance 1' and 2 administered per single dose mentioned by way of example correspond to the following quantities of 1 and 2 administered per single dose: 20 μg of 1 and 25 μg of 2, 20 μg of 1 and 50 μg of 2, 20 μg of 1 and 100 μg of 2, 20 μg of 1 and 150 μg of 2, 20 μg of 1 and 200 μg of 2, 20 μg of 1 and 250 μg of 2, 40 μg of 1 and 25 μg of 2, 40 μg of 1 and 25 μg of 2, 40 μg of 1 and 50 μg of 2, 40 μg of 1 and 100 μg of 2, 40 μg of 1 and 150 μg of 2, 40 μg of 1 and 200 μg of 2, 40 μg of 1 and 250 μg of 2, 60 μg of 1 and 25 μg of 2, 60 μg of 1 and 50 μg of 2, 60 μg of 1 and 100 μg of 2, 60 μg of 1 and 150 μg of 2, 60 μg of 1 and 200 μg of 2, 60 μg of 1 and 250 μg of 2, 100 μg of 1 and 25 μg of 2, 100 μg of 1 and 50 μg of 2, 100 μg of 1 and 100 μg of 2, 100 μg of 1 and 150 μg of 2, 100 μg of 1 and 200 μg of 2, 100 g of 1 and 250 μg of 2, 200 μg of 1 and 25 μg of 2, 200 μg of 1 and 50 μg of 2, 200 μg of 1 and 100 μg of 2, 200 μg of 1 and 150 μg of 2, 200 μg of 1 and 200 μg of 2, 200 μg of 1 and 250 μg of 2, 250 μg of 1 and 25 μg of 2, 250 μg of 1 and 50 μg of 2, 250 μg of 1 and 100 μg of 2, 250 μg of 1 and 150 μg of 2, 250 μg of 1 and 200 μg of 2, 250 μg of 1 and 250 μg of 2, 500 μg of 1 and 25 μg of 2, 500 μg of 1 and 50 μg of 2, 500 μg of 1 and 100 μg of 2, 500 μg of 1 and 150 μg of 2, 500 μg of 1 and 200 μg of 2, or 500 μg of 1 and 250 μg of 2.

The active substance combinations of 1 and 2 according to the invention are preferably administered by inhalation. For this purpose, ingredients 1 and 2 have to be made available in forms suitable for inhalation. Inhalable preparations according to the invention include inhalable powders, propellant-containing metered dose aerosols, or propellant-free inhalable solutions. Inhalable powders according to the invention containing the combination of active substances 1 and 2 may consist of the active substances on their own or of a mixture of the active substances with physiologically acceptable excipients. Within the scope of the present invention, the term carrier may optionally be used instead of the term excipient. Within the scope of the present invention, the term propellant-free inhalable solutions also includes concentrates or sterile inhalable solutions ready for use. The preparations according to the invention may contain the combination of active substances 1 and 2 either together in one formulation or in two separate formulations. These formulations which may be used within the scope of the present invention are described in more detail in the next part of the specification.

A. Inhalable Powder Containing the Combinations of Active Substances 1 and 2 According to the Invention The inhalable powders according to the invention may contain 1 and 2 either on their own or in admixture with suitable physiologically acceptable excipients.

If the active substances 1 and 2 are present in admixture with physiologically acceptable excipients, the following physiologically acceptable excipients may be used to prepare these inhalable powders according to the invention: monosaccharides (e.g., glucose or arabinose), disaccharides (e.g., lactose, saccharose, maltose, or trehalose), oligo- and polysaccharides (e.g., dextran), polyalcohols (e.g., sorbitol, mannitol, or xylitol), salts (e.g., sodium chloride or calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 μm, preferably between 10 μm and 150 μm, most preferably between 15 μm and 80 μm. It may sometimes seem appropriate to add finer excipient fractions with an average particle size of 1 μm to 9 μm to the excipient mentioned above. These finer excipients are also selected from the group of possible excipients listed hereinbefore. Finally, in order to prepare the inhalable powders according to the invention, micronised active substance 1 and 2, preferably with an average particle size of 0.5 μm to 10 μm, more preferably from 1 μm to 5 μm, is added to the excipient mixture. Processes for producing the inhalable powders according to the invention by grinding and micronizing and by finally mixing the ingredients together are known from the prior art. The inhalable powders according to the invention may be prepared and administered either in the form of a single powder mixture which contains both 1 and 2 or in the form of separate inhalable powders which contain only 1 or 2.

The inhalable powders according to the invention may be administered using inhalers known from the prior art. Inhalable powders according to the invention which contain one or more physiologically acceptable excipients in addition to 1 and 2 may be administered, for example, by means of inhalers which deliver a single dose from a supply using a measuring chamber as described in U.S. Pat. No. 4,570,630, or by other means as described in DE 36 25 685 A. Preferably, the inhalable powders according to the invention which contain physiologically acceptable excipients in addition to 1 and 2 are packed into capsules (to produce so-called inhalettes) which are used in inhalers as described, for example, in WO 94/28958.

A particularly preferred inhaler for using the pharmaceutical combination according to the invention in inhalettes is shown in FIG. 1.

This inhaler (HANDIHALER®) for inhaling powdered pharmaceutical compositions from capsules is characterized by a housing 1 containing two windows 2, a deck 3 in which there are air inlet ports and which is provided with a screen 5 secured via a screen housing 4, an inhalation chamber 6 connected to the deck 3 on which there is a push button 8 provided with two sharpened pins 7 and movable counter to a spring 8, and a mouthpiece 12 which is connected to the housing 1, the deck 3 and a cover 11 via a spindle 10 to enable it to be flipped open or shut, as well as air holes 13 for adjusting the flow resistance.

If the inhalable powders according to the invention are packed into capsules (inhalers) for the preferred use described above, the quantities packed into each capsule should be 1 mg to 30 mg, preferably 3 mg to 20 mg, more particularly 5 mg to 10 mg of inhalable powder per capsule. These capsules contain, according to the invention, either together or separately, the doses of 1 or 1' and 2 mentioned hereinbefore for each single dose.

B. Propellant Gas-Driven Inhalation Aerosols Containing the Combinations of Active Substances 1 and 2

Inhalation aerosols containing propellant gas according to the invention may contain substances 1 and 2 dissolved in the propellant gas or in dispersed form. 1 and 2 may be present in separate formulations or in a single preparation, in which 1 and 2 are either both dissolved, both dispersed, or only one component is dissolved and the other is dispersed. The propellant gases which may be used to prepare the inhalation aerosols according to the invention are known from the prior art. Suitable propellant gases are selected from among hydrocarbons such as n-propane, n-butane or isobutane and halohydrocarbons such as fluorinated derivatives of methane, ethane, propane, butane, cyclopropane, or cyclobutane. The propellant gases mentioned above may be used on their own or in mixtures thereof. Particularly preferred propellant gases are halogenated alkane derivatives selected from TG12, TG134a (1,1,1,2-tetrafluoroethane), and TG227 (1,1,1,2,3,3,3-heptafluoropropane) and mixtures thereof, of which the propellant gases TG134a, TG227, and mixtures thereof are preferred.

The propellant-driven inhalation aerosols according to the invention may also contain other ingredients such as co-solvents, stabilizers, surfactants, antioxidants, lubricants, preservatives, and pH adjusters. All these ingredients are known in the art.

The inhalation aerosols containing propellant gas according to the invention may contain up to 5 wt.-% of active substance 1 and/or 2. Aerosols according to the invention contain, for example, 0.002 to 5 wt.-%, 0.01 to 3 wt.-%, 0.015 to 2 wt.-%, 0.1 to 2 wt.-%, 0.5 to 2 wt.-%, or 0.5 to 1 wt.-% of active substance 1 and/or 2.

If the active substances 1 and/or 2 are present in dispersed form, the particles of active substance preferably have an average particle size of up to 10 µm, preferably from 0.1 µM to 6 µm, more preferably from 1 µm to 5 µm.

The propellant-driven inhalation aerosols according to the invention mentioned above may be administered using inhalers known in the art, such as metered dose inhalers (MDIs). Accordingly, in another aspect, the present invention relates to pharmaceutical compositions in the form of propellant-driven aerosols as hereinbefore described combined with one or more inhalers suitable for administering these aerosols. In addition, the present invention relates to inhalers which are characterized in that they contain the propellant gas-containing aerosols described above according to the invention. The present invention also relates to cartridges which are fitted with a suitable valve and can be used in a suitable inhaler and which contain one of the above-mentioned propellant gas-containing inhalation aerosols according to the invention. Suitable cartridges and methods of filling these cartridges with the inhalable aerosols containing propellant gas according to the invention are known from the prior art.

C. Propellant-Free Inhalable Solutions or Suspensions Containing the Combinations of Active Substances 1 and 2 According to the Invention Propellant-free inhalable solutions and suspensions according to the invention contain, for example, aqueous or alcoholic, preferably ethanolic solvents, optionally ethanolic solvents mixed with aqueous solvents. If aqueous/ethanolic solvent mixtures are used the relative proportion of ethanol compared with water is not limited but the maximum is up to 70 percent by volume, more particularly up to 60 percent by volume and most preferably up to 30 percent by volume. The remainder of the volume is made up of water. The solutions or suspensions containing 1 and 2, separately or together, are adjusted to a pH of 2 to 7, preferably 2 to 5, using suitable acids. The pH may be adjusted using acids selected from inorganic or organic acids. Examples of suitable inorganic acids include hydrochloric acid, hydrobromic acid, nitric acid, sulfuric acid, and/or phosphoric acid. Examples of particularly suitable organic acids include ascorbic acid, citric acid, malic acid, tartaric acid, maleic acid, succinic acid, fumaric acid, acetic acid, formic acid, and/or propionic acid etc. Preferred inorganic acids are hydrochloric and sulfuric acids. It is also possible to use the acids which have already formed an acid addition salt with one of the active substances. Of the organic acids, ascorbic acid, fumaric acid, and citric acid are preferred. If desired, mixtures of the above acids may be used, particularly in the case of acids which have other properties in addition to their acidifying qualities, e.g., as flavorings, antioxidants or complexing agents, such as citric acid or ascorbic acid, for example. According to the invention, it is particularly preferred to use hydrochloric acid to adjust the pH.

According to the invention, the addition of edetic acid (EDTA) or one of the known salts thereof, sodium edetate, as stabilizer or complexing agent is unnecessary in the present formulation. Other embodiments may contain this compound or these compounds. In a preferred embodiment the content based on sodium edetate is less than 100 mg/100 mL, preferably less than 50 mg/100 mL, more preferably less than 20 mg/100 mL. Generally, inhalable solutions in which the content of sodium edetate is from 0 to 10 mg/100 mL are preferred.

Co-solvents and/or other excipients may be added to the propellant-free inhalable solutions according to the invention. Preferred co-solvents are those which contain hydroxyl groups or other polar groups, e.g., alcohols, particularly isopropyl alcohol, glycols, particularly propyleneglycol, polyethyleneglycol, polypropyleneglycol, glycol ether, glycerol, polyoxyethylene alcohols, and polyoxyethylene fatty acid esters. The terms excipients and additives in this context denote any pharmacologically acceptable substance which is not an active substance but which can be formulated with the active substance or substances in the physiologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilizers, complexing agents, antioxidants, and/or preservatives which guarantee or prolong the shelf life of the finished pharmaceutical formulation, flavorings, vitamins, and/or other additives known in the art. The additives also include pharmacologically acceptable salts such as sodium chloride as isotonic agents.

The preferred excipients include antioxidants such as ascorbic acid, for example, provided that it has not already been used to adjust the pH, vitamin A, vitamin E, tocopherols, and similar vitamins and provitamins occurring in the human body.

Preservatives may be used to protect the formulation from contamination with pathogens. Suitable preservatives are those which are known in the art, particularly cetyl pyridinium chloride, benzalkonium chloride, or benzoic acid or benzoates such as sodium benzoate in the concentration known from the prior art. The preservatives mentioned above are preferably present in concentrations of up to 50 mg/100 mL, more preferably between 5 and 20 mg/100 mL.

Preferred formulations contain, in addition to the solvent water and the combination of active substances 1 and 2, only benzalkonium chloride and sodium edetate. In another preferred embodiment, no sodium edetate is present.

The propellant-free inhalable solutions according to the invention are administered in particular using inhalers of the kind which are capable of nebulizing a small amount of a liquid formulation in the therapeutic dose within a few seconds to produce an aerosol suitable for therapeutic inhalation. Within the scope of the present invention, preferred inhalers are those in which a quantity of less than 100 µL, preferably less than 50 µL, more preferably between 20 µL and 30 µL of active substance solution can be nebulized in preferably one spray action to form an aerosol with an average particle size of less than 20 µm, preferably less than 10 µm, in such a way that the inhalable part of the aerosol corresponds to the therapeutically effective quantity.

An apparatus of this kind for propellant-free delivery of a metered quantity of a liquid pharmaceutical composition for inhalation is described for example in International Patent Application WO 91/14468 and also in WO 97/12687 (cf in particular FIGS. 6a and 6b). The nebulizers (devices) described therein are known by the name RESPIMAT®.

This RESPIMAT® nebulizer can advantageously be used to produce the inhalable aerosols according to the invention containing the combination of active substances 1 and 2. Because of its cylindrical shape and handy size of less than 9 cm to 15 cm long and 2 cm to 4 cm wide, this device can be carried at all times by the patient. The nebulizer sprays a defined volume of pharmaceutical formulation using high pressures through small nozzles so as to produce inhalable aerosols.

The preferred atomizer essentially consists of an upper housing part, a pump housing, a nozzle, a locking mechanism, a spring housing, a spring and a storage container, characterized by:
 a pump housing which is secured in the upper housing part and which comprises at one end a nozzle body with the nozzle or nozzle arrangement;
 a hollow plunger with valve body;
 a power takeoff flange in which the hollow plunger is secured and which is located in the upper housing part;
 a locking mechanism situated in the upper housing part;
 a spring housing with the spring contained therein, which is rotatably mounted on the upper housing part by means of a rotary bearing; and
 a lower housing part which is fitted onto the spring housing in the axial direction.

The hollow plunger with valve body corresponds to a device disclosed in WO 97/12687. It projects partially into the cylinder of the pump housing and is axially movable within the cylinder. Reference is made in particular to FIGS. 1 to 4, especially FIG. 3, and the relevant parts of the description. The hollow plunger with valve body exerts a pressure of 5 MPa to 60 MPa (about 50 bar to 600 bar), preferably 10 MPa to 60 MPa (about 100 bar to 600 bar) on the fluid, the measured amount of active substance solution, at its high pressure end at the moment when the spring is actuated. Volumes of 10 µL to 50 µL are preferred, while volumes of 10 µL to 20 µL are particularly preferred and a volume of 15 µL per spray is most particularly preferred.

The valve body is preferably mounted at the end of the hollow plunger facing the valve body.

The nozzle in the nozzle body is preferably microstructured, i.e., produced by microtechnology. Microstructured nozzle bodies are disclosed for example in WO-94/07607; reference is hereby made to the contents of this specification, particularly FIG. 1 therein and the associated description.

The nozzle body consists, for example, of two sheets of glass and/or silicon firmly joined together, at least one of which has one or more microstructured channels which connect the nozzle inlet end to the nozzle outlet end. At the nozzle outlet end there is at least one round or non-round opening 2 to 10 microns deep and 5 to 15 microns wide, the depth preferably being 4.5 to 6.5 microns while the length is preferably 7 to 9 microns.

In the case of a plurality of nozzle openings, preferably two, the directions of spraying of the nozzles in the nozzle body may extend parallel to one another or may be inclined relative to one another in the direction of the nozzle opening. In a nozzle body with at least two nozzle openings at the outlet end the directions of spraying may be at an angle of 20° to 160° to one another, preferably 60° to 150°, most preferably 80° to 100°. The nozzle openings are preferably arranged at a spacing of 10 to 200 microns, more preferably at a spacing of 10 to 100 microns, most preferably 30 to 70 microns. Spacings of 50 microns are most preferred. The directions of spraying will therefore meet in the vicinity of the nozzle openings.

The liquid pharmaceutical preparation strikes the nozzle body with an entry pressure of up to 600 bar, preferably 200 bar to 300 bar, and is atomized into an inhalable aerosol through the nozzle openings. The preferred particle or droplet sizes of the aerosol are up to 20 microns, preferably 3 to 10 microns.

The locking mechanism contains a spring, preferably a cylindrical helical compression spring, as a store for the mechanical energy. The spring acts on the power takeoff flange as an actuating member the movement of which is determined by the position of a locking member. The travel of the power takeoff flange is precisely limited by an upper and lower stop. The spring is preferably biased, via a power step-up gear, e.g., a helical thrust gear, by an external torque which is produced when the upper housing part is rotated counter to the spring housing in the lower housing part. In this case, the upper housing part and the power takeoff flange have a single or multiple V-shaped gear.

The locking member with engaging locking surfaces is arranged in a ring around the power takeoff flange. It consists, for example, of a ring of plastic or metal which is inherently radially elastically deformable. The ring is arranged in a plane at right angles to the atomizer axis. After the biasing of the spring, the locking surfaces of the locking member move into the path of the power takeoff flange and prevent the spring from relaxing. The locking member is actuated by means of a button. The actuating button is connected or coupled to the locking member. In order to actuate the locking mechanism, the actuating button is moved parallel to the annular plane, preferably into the atomizer; this causes the deformable ring to deform in the annual plane. Details of the construction of the locking mechanism are given in WO 97/20590.

The lower housing part is pushed axially over the spring housing and covers the mounting, the drive of the spindle and the storage container for the fluid.

When the atomizer is actuated the upper housing part is rotated relative to the lower housing part, the lower housing part taking the spring housing with it. The spring is thereby compressed and biased by means of the helical thrust gear and the locking mechanism engages automatically. The angle of rotation is preferably a whole-number fraction of 360°, e.g., 180°. At the same time as the spring is biased, the power takeoff part in the upper housing part is moved along by a given distance, the hollow plunger is withdrawn inside the cylinder in the pump housing, as a result of which some of the fluid is sucked out of the storage container and into the high pressure chamber in front of the nozzle.

If desired, a number of exchangeable storage containers which contain the fluid to be atomized may be pushed into the atomizer one after another and used in succession. The storage container contains the aqueous aerosol preparation according to the invention.

The atomizing process is initiated by pressing gently on the actuating button. As a result, the locking mechanism opens up the path for the power takeoff member. The biased spring pushes the plunger into the cylinder of the pump housing. The fluid leaves the nozzle of the atomizer in atomized form.

Further details of construction are disclosed in PCT Applications WO 97/12683 and WO 97/20590, to which reference is hereby made.

The components of the atomizer (nebulizer) are made of a material which is suitable for its purpose. The housing of the atomizer and, if its operation permits, other parts as well are preferably made of plastics, e.g., by injection molding. For medicinal purposes, physiologically safe materials are used.

Figure 2A:
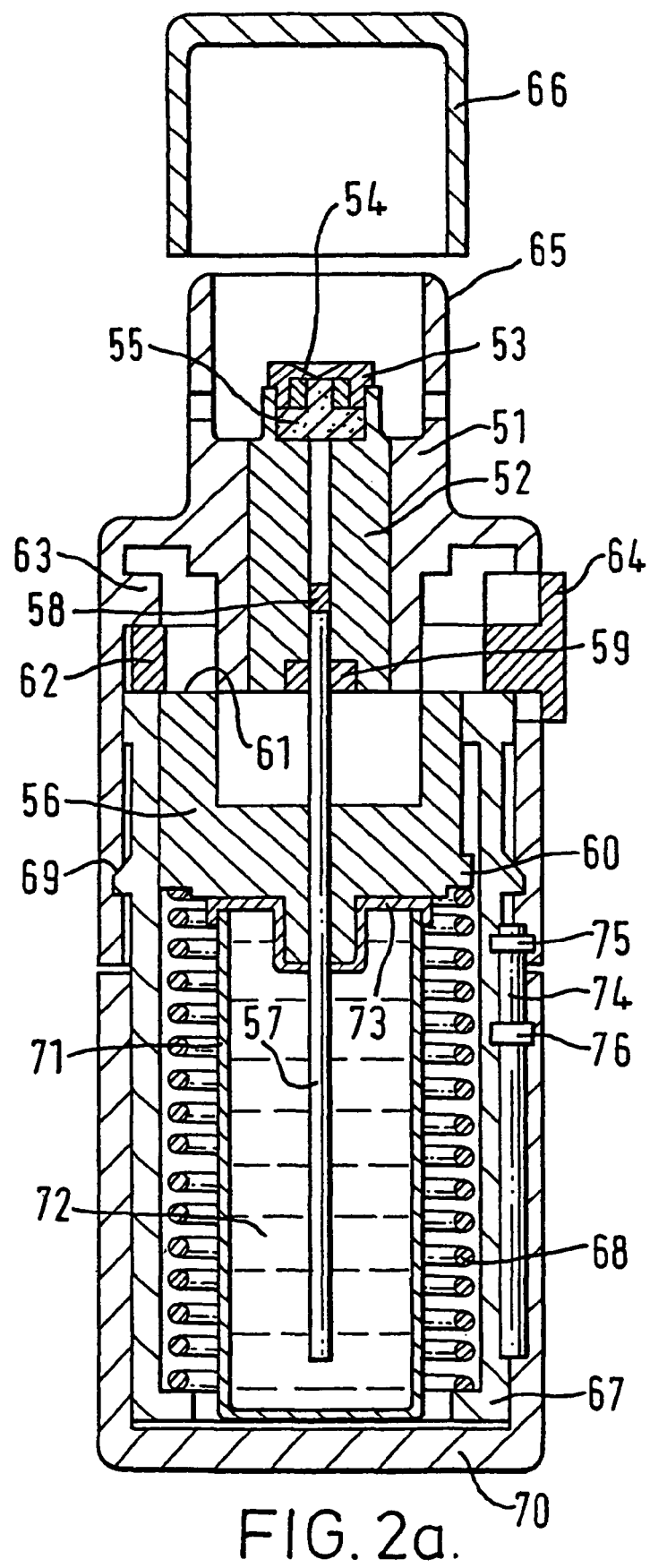
FIGS. 2a and 2b illustrate a nebulizer that can used to inhale aqueous aerosol preparations according to the present invention.

FIGS. 2a/b attached to this patent application, which are identical to FIGS. 6a/b of WO 97/12687, show the nebulizer (RESPIMAT®) which can advantageously be used for inhaling the aqueous aerosol preparations according to the invention.

Figure 2B:
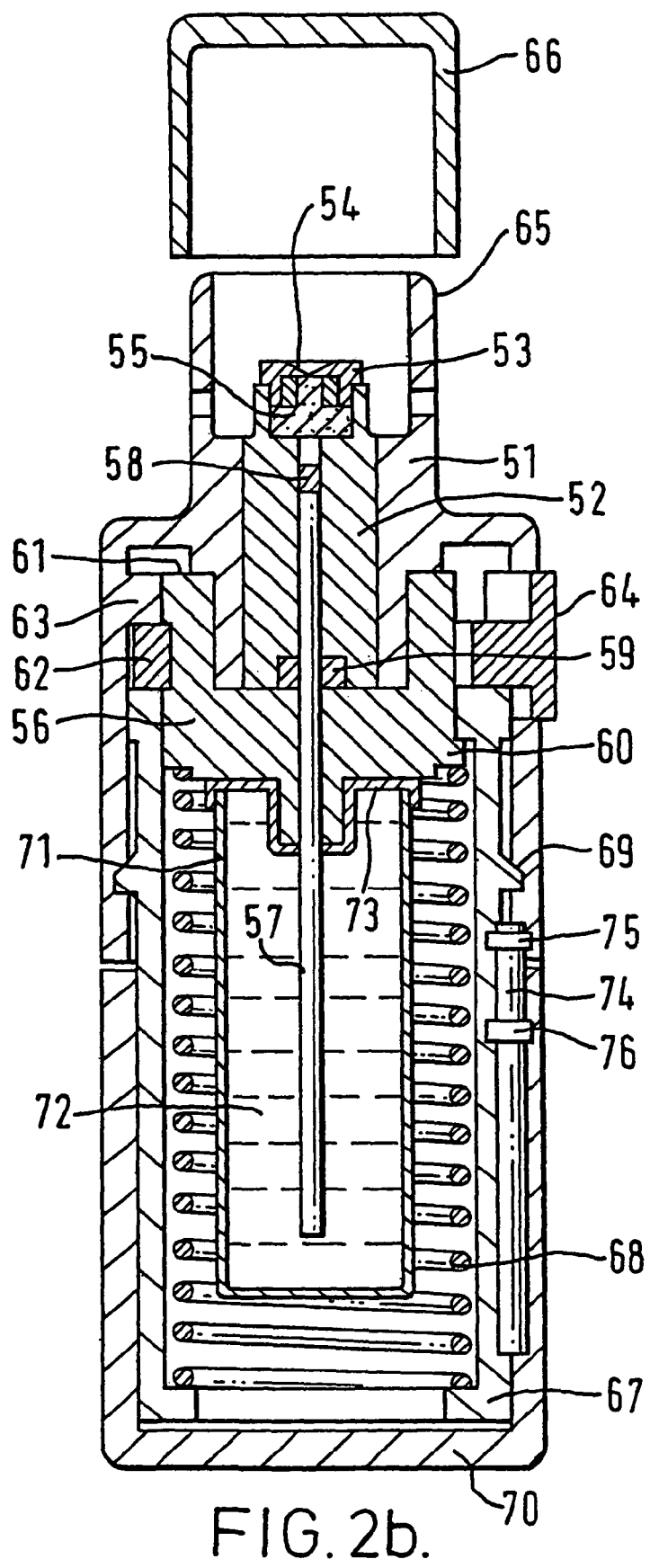

FIG. 2a shows a longitudinal section through the atomizer with the spring biased while FIG. 2b shows a longitudinal section through the atomizer with the spring relaxed.

The upper housing part (51) contains the pump housing (52) on the end of which is mounted the holder (53) for the atomizer nozzle. In the holder is the nozzle body (54) and a filter (55). The hollow plunger (57) fixed in the power takeoff flange (56) of the locking mechanism projects partially into the cylinder of the pump housing. At its end the hollow plunger carries the valve body (58). The hollow plunger is sealed off by means of the seal (59). Inside the upper housing part is the stop (60) on which the power takeoff flange abuts when the spring is relaxed. On the power takeoff flange is the stop (61) on which the power takeoff flange abuts when the spring is biased. After the biasing of the spring the locking member (62) moves between the stop (61) and a support (63) in the upper housing part. The actuating button (64) is connected to the locking member. The upper housing part ends in the mouthpiece (65) and is sealed off by means of the protective cover (66) which can be placed thereon.

The spring housing (67) with compression spring (68) is rotatably mounted on the upper housing part by means of the snap-in lugs (69) and rotary bearing. The lower housing part (70) is pushed over the spring housing. Inside the spring housing is the exchangeable storage container (71) for the fluid (72) which is to be atomized. The storage container is sealed off by the stopper (73) through which the hollow plunger projects into the storage container and is immersed at its end in the fluid (supply of active substance solution).

The spindle (74) for the mechanical counter is mounted in the covering of the spring housing. At the end of the spindle facing the upper housing part is the drive pinion (75). The slider (76) sits on the spindle.

The nebulizer described above is suitable for nebulizing the aerosol preparations according to the invention to produce an aerosol suitable for inhalation.

If the formulation according to the invention is nebulized using the method described above (RESPIMAT®) the quantity delivered should correspond to a defined quantity with a tolerance of not more than 25%, preferably 20% of this amount in at least 97%, preferably at least 98% of all operations of the inhaler (spray actuations). Preferably, between 5 and 30 mg of formulation, most preferably between 5 and 20 mg of formulation are delivered as a defined mass on each actuation.

However, the formulation according to the invention may also be nebulized by means of inhalers other than those described above, e.g., jet stream inhalers.

Accordingly, in a further aspect, the invention relates to pharmaceutical formulations in the form of propellant-free inhalable solutions or suspensions as described above combined with a device suitable for administering these formulations, preferably in conjunction with the RESPIMAT® nebulizer. Preferably, the invention relates to propellant-free inhalable solutions or suspensions characterized by the combination of active substances 1 and 2 according to the invention in conjunction with the device known by the name RESPIMAT®. In addition, the present invention relates to the above-mentioned devices for inhalation, preferably the RESPIMAT® nebulizer, characterized in that they contain the propellant-free inhalable solutions or suspensions according to the invention as described hereinbefore.

The propellant-free inhalable solutions or suspensions according to the invention may take the form of concentrates or sterile inhalable solutions or suspensions ready for use, as well as the above-mentioned solutions and suspensions designed for use in a RESPIMAT® nebulizer. Formulations ready for use may be produced from the concentrates, for example, by the addition of isotonic saline solutions. Sterile formulations ready for use may be administered using energy-operated free-standing or portable nebulizers which produce inhalable aerosols by means of ultrasound or compressed air by the Venturi principle or other principles.

Accordingly, in another aspect, the present invention relates to pharmaceutical compositions in the form of propellant-free inhalable solutions or suspensions as described hereinbefore which take the form of concentrates or sterile formulations ready for use, combined with a device suitable for administering these solutions, characterized in that the device is an energy-operated free-standing or portable nebulizer which produces inhalable aerosols by means of ultrasound or compressed air by the Venturi principle or other methods.

The Examples which follow serve to illustrate the present invention in more detail without restricting the scope of the invention to the following embodiments by way of example.

First, the preparation of compounds 1 used within the scope of the present invention which are not known in the art will be described.

Preparation of the Compounds of Formula 1

1.a. 2,2-Diphenylpropionic acid chloride 52.08 g (0.33 mol) of oxalyl chloride are slowly added dropwise at 20° C. to a suspension of 25.0 g (0.11 mol) of 2,2-diphenylpropionic acid, 100 mL of dichloromethane, and 4 drops of dimethylformamide. The mixture is stirred for 1 hour at 20° C. and 0.5 hour at 50° C. The solvent is distilled off and the residue remaining is used in the next step without any further purification.

1.b. scopine 2,2-diphenylpropionate

The residue obtained from step 1.a. is dissolved in 100 mL of dichloromethane and at 40° C. a solution of 51.45 g (0.33 mol) of scopine in 200 mL of dichloromethane is added dropwise thereto. The resulting suspension is stirred for 24 hours at 40° C., then the precipitate formed is suction filtered, and the filtrate is extracted first with water, then with aqueous hydrochloric acid. The combined aqueous phases are made alkaline with aqueous sodium carbonate solution, extracted with dichloromethane, the organic phase is dried over $Na_2SO_4$, evaporated to dryness, and the hydrochloride is precipitated from the residue. The product is purified by recrystallization from acetonitrile. Yield: 20.85 g (47% of theory); DC: $R_f$ value: 0.24 (eluent: sec-butanol/formic acid/water 75:15:10); m.p.: 203° C.-204° C.

1.c. scopine 2,2-diphenylpropionate methobromide 11.98 g (0.033 mol) of the compound of step 1.b., 210 mL of acetonitrile, 70 mL of dichloromethane, and 20.16 g (0.1 mol) of 46.92% bromomethane in acetonitrile are combined at 20° C. and left to stand for 3 days. The solution is evaporated to dryness and the residue is recrystallized from isopropanol. Yield: 11.34 g (75% of theory); m.p.: 208° C.-209° C. $C_{24}H_{28}NO_3xBr$ (458.4); elemental analysis: calculated: C (62.89), H (6.16), N (3.06); found: C (62.85), H (6.12), N (3.07).

The salts 1 wherein $X^-$ denotes an anion with a single negative charge other than bromide may be obtained in a manner similar to step 1.3.

The following examples of formulations, which may be obtained analogously to methods known in the art, serve to illustrate the present invention more fully without restricting it to the contents of these examples.

EXAMPLES OF FORMULATIONS

A. Inhalable Powders

EXAMPLE 1

| Ingredients | μg per capsule |
|---|---|
| 1'-bromide | 100 |
| budesonide | 200 |
| lactose | 4700 |
| Total | 5000 |

EXAMPLE 2

| Ingredients | μg per capsule |
|---|---|
| 1'-bromide | 100 |
| fluticasone propionate | 125 |
| lactose | 4775 |
| Total | 5000 |

EXAMPLE 3

| Ingredients | μg per capsule |
|---|---|
| 1'-bromide | 100 |
| mometasone furoate × $H_2O$ | 250 |
| lactose | 4650 |
| Total | 5000 |

EXAMPLE 4

| Ingredients | μg per capsule |
|---|---|
| 1'-bromide | 100 |
| ciclesonide | 250 |
| lactose | 4650 |
| Total | 5000 |

EXAMPLE 5

| Ingredients | μg per capsule |
|---|---|
| 1'-bromide | 50 |
| budesonide | 125 |
| lactose | 4825 |
| Total | 5000 |

EXAMPLE 6

| Ingredients | μg per capsule |
|---|---|
| 1'-bromide | 50 |
| fluticasone propionate | 200 |
| lactose | 4750 |
| Total | 5000 |

EXAMPLE 7

| Ingredients | μg per capsule |
|---|---|
| 1'-bromide | 75 |
| mometasone furoate × $H_2O$ | 250 |
| lactose | 4675 |
| Total | 5000 |

EXAMPLE 8

| Ingredients | μg per capsule |
|---|---|
| 1'-bromide | 75 |
| ciclesonide | 250 |
| lactose | 4675 |
| Total | 5000 |

EXAMPLE 9

| Ingredients | μg per capsule |
|---|---|
| 1'-bromide | 100 |
| ST-126 | 250 |
| lactose | 4650 |
| Total | 5000 |

EXAMPLE 10

| Ingredients | μg per capsule |
|---|---|
| 1'-bromide | 50 |
| ST-126 | 125 |
| lactose | 4825 |
| Total | 5000 |

B. Propellant-Containing Aerosols for Inhalation

EXAMPLE 11

Suspension Aerosol

| Ingredients | % by weight |
|---|---|
| 1'-bromide | 50 |
| budesonide | 0.4 |
| soya lecithin | 0.2 |
| TG 134a:TG227 (2:3) | to 100 |

EXAMPLE 12

Suspension Aerosol

| Ingredients | % by weight |
|---|---|
| 1'-bromide | 0.020 |
| fluticasone propionate | 0.3 |
| isopropyl myristate | 0.1 |
| TG 227 | to 100 |

EXAMPLE 13

Suspension Aerosol

| Ingredients | % by weight |
|---|---|
| 1'-bromide | 0.020 |
| mometasone furoate × $H_2O$ | 0.6 |
| isopropyl myristate | 0.1 |
| TG 227 | to 100 |

EXAMPLE 14

Suspension Aerosol

| Ingredients | % by weight |
|---|---|
| 1'-bromide | 0.020 |
| ciclesonide | 0.4 |
| isopropyl myristate | 0.1 |
| TG 134a:TG227 (2:3) | to 100 |

EXAMPLE 15

Suspension Aerosol

| Ingredients | % by weight |
|---|---|
| 1'-bromide | 0.039 |
| ciclesonide | 0.4 |
| absolute ethanol | 0.5 |
| isopropyl myristate | 0.1 |
| TG 134a:TG227 (2:3) | to 100 |

EXAMPLE 16

Solution Aerosol

| Ingredients | % by weight |
|---|---|
| 1'-bromide | 0.039 |
| fluticasone propionate | 0.2 |
| absolute ethanol | 0.5 |
| isopropyl myristate | 0.1 |
| TG 134a:TG227 (2:3) | to 100 |

EXAMPLE 17

Solution Aerosol

| Ingredients | % by weight |
|---|---|
| 1'-bromide | 0.039 |
| mometasone furoate × $H_2O$ | 0.6 |
| absolute ethanol | 0.5 |
| isopropyl myristate | 0.1 |
| TG 134a:TG227 (2:3) | to 100 |

EXAMPLE 18

Solution Aerosol

| Ingredients | % by weight |
|---|---|
| 1'-bromide | 0.039 |
| ciclesonide | 0.4 |
| absolute ethanol | 0.5 |
| isopropyl myristate | 0.1 |
| TG 134a:TG227 (2:3) | to 100 |

EXAMPLE 19

Solution Aerosol

| Ingredients | % by weight |
|---|---|
| 1'-bromide | 0.039 |
| ST-126 | 0.6 |
| absolute ethanol | 0.5 |
| isopropyl myristate | 0.1 |
| TG 134a:TG227 (2:3) | to 100 |

EXAMPLE 20

Solution Aerosol

| Ingredients | % by weight |
|---|---|
| 1'-bromide | 0.039 |
| ST-126 | 0.4 |
| absolute ethanol | 0.5 |

EXAMPLE 20-continued

| Solution Aerosol | |
|---|---|
| Ingredients | % by weight |
| isopropyl myristate | 0.1 |
| TG 134a:TG227 (2:3) | to 100 |

We claim:

1. A method of treating asthma or COPD in a patient in need thereof, the method comprising administering an effective amount of:

(a) a salt of formula 1

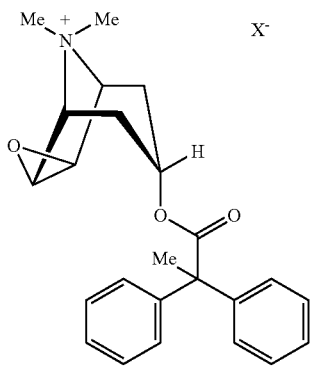

wherein $X^-$ is an anion with a single negative charge; and (b) a steroid 2.

2. The method according to claim 1, wherein the salt of formula 1 and the steroid 2 are in the form of a pharmaceutical composition.

3. The method according to claim 1, wherein a salt of formula 1 and the steroid 2 are administered once a day.

4. The method according to claim 2, wherein the pharmaceutical composition is administered once a day.

5. The method according to claim 1, wherein $X^-$ is selected from chloride, bromide, iodide, sulfate, phosphate, methanesulfonate, nitrate, maleate, acetate, citrate, fumarate, tartrate, oxalate, succinate, benzoate, and p-toluenesulfonate.

6. The method according to claim 1, wherein the steroid 2 is selected from flunisolide, beclomethasone, triamcinolone, budesonide, fluticasone, mometasone, ciclesonide, rofleponide, ST-126, and dexamethasone.

7. The method according to claim 6, wherein the steroid 2 is selected from budesonide, fluticasone, mometasone, ciclesonide, and ST-126.

8. The method according to claim 1, wherein the salt of formula 1 and the steroid 2 are administered by inhalation.

9. The method according to claim 2, wherein the pharmaceutical composition is administered by inhalation.

10. The method according to claim 9, wherein the pharmaceutical composition is an inhalable powder, a propellant-containing metered-dose aerosol, or a propellant-free inhalable solution or suspension.

11. The method according to claim 10, wherein the pharmaceutical composition is an inhalable powder comprising the salt of formula 1 and the steroid 2 in admixture with a physiologically acceptable excipient selected from monosaccharides, disaccharides, oligo- and polysaccharides, polyalcohols, salts, or mixtures thereof.

12. The method according to claim 11, wherein the excipient has a maximum average particle size of 250 µm or less.

13. The method according to claim 12, wherein the excipient has a maximum average particle size of between 10 µm and 150 µm.

14. The method according to claim 10, wherein the pharmaceutical composition is a propellant-containing metered-dose aerosol comprising the salt of formula 1 and the steroid 2 in dissolved or dispersed form.

15. The method according to claim 14, wherein the propellant is a hydrocarbon or halohydrocarbon.

16. The method according to claim 10, wherein the pharmaceutical composition is a propellant-free inhalable solution or suspension further comprising a solvent selected from water, ethanol, or a mixture thereof.

* * * * *